(12) United States Patent
Wiggli et al.

(10) Patent No.: US 7,575,937 B2
(45) Date of Patent: Aug. 18, 2009

(54) DEVICE AND METHOD FOR DISPOSING PIPETTE SYRINGES IN A SYSTEM USED FOR MANIPULATING LIQUID SAMPLES

(75) Inventors: Markus Wiggli, Tann (CH); Fred Schinzel, Männedorf (CH); Bronwen Forster, Männedorf (CH)

(73) Assignee: Tecan Trading AG, Männedorf (CH)

( * ) Notice: Subject to any disclaimer, the term of this patent is extended or adjusted under 35 U.S.C. 154(b) by 367 days.

(21) Appl. No.: 11/630,181

(22) PCT Filed: May 30, 2005

(86) PCT No.: PCT/CH2005/000305
§ 371 (c)(1),
(2), (4) Date: Feb. 13, 2007

(87) PCT Pub. No.: WO2006/000115
PCT Pub. Date: Jan. 5, 2006

(65) Prior Publication Data
US 2007/0264725 A1    Nov. 15, 2007

(30) Foreign Application Priority Data
Jun. 24, 2004   (CH) .................................... 1067/04

(51) Int. Cl.
*G01N 35/10*   (2006.01)

(52) U.S. Cl. ...................................... 436/180; 422/100
(58) Field of Classification Search ....................... None
See application file for complete search history.

(56) References Cited

U.S. PATENT DOCUMENTS

| | | | |
|---|---|---|---|
| 7,169,362 B2* | 1/2007 | Toi et al. ..................... | 422/102 |
| 2001/0036425 A1* | 11/2001 | Gazeau et al. .............. | 422/100 |
| 2003/0026738 A1* | 2/2003 | Everett ........................ | 422/100 |

* cited by examiner

*Primary Examiner*—Yelena G Gakh
*Assistant Examiner*—Dirk Bass
(74) *Attorney, Agent, or Firm*—Notaro & Michalos P.C.

(57) ABSTRACT

A device and method for situating pipette or dispenser tips in a system for manipulating liquid samples, has a robot manipulator for orienting the tips relative to sample containers, drives for moving the robot manipulator and processors for controlling movements and actions of the robot manipulator and/or the tips. At least two tips are situated at an axial distance from each another, on at least two blocks on an arm of the robot manipulator. The axial distance corresponds to a grid spacing of wells of a microplate. At least one of the blocks is individually movable in an X direction and in a Y direction. The method allows time-saving pipetting over of liquid samples between diverse sample containers, such as between sample tubes and microplates having 24, 96, 384, or 1536 wells.

16 Claims, 5 Drawing Sheets

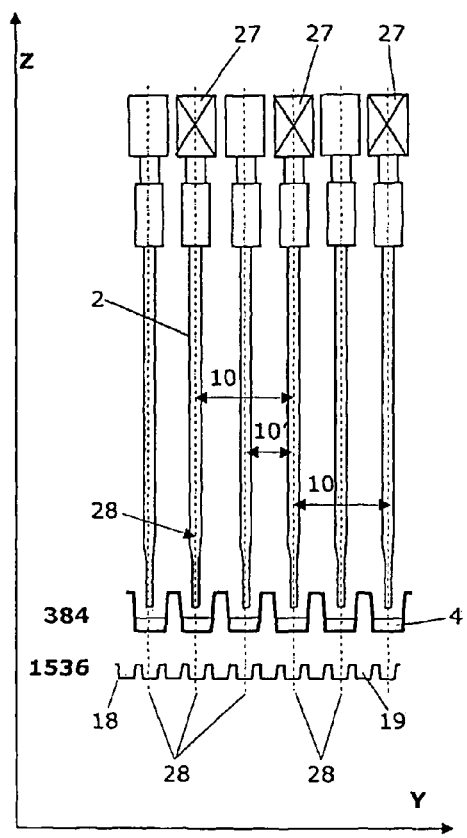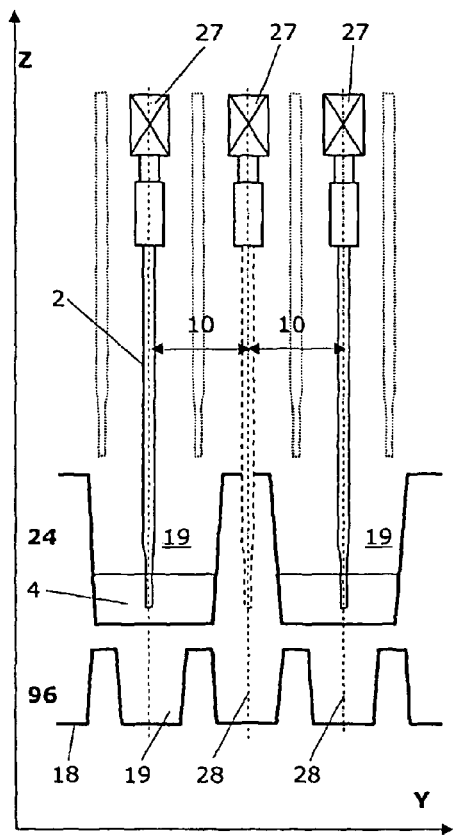

DEVICE AND METHOD FOR DISPOSING PIPETTE SYRINGES IN A SYSTEM USED FOR MANIPULATING LIQUID SAMPLES

RELATED PATENT APPLICATIONS

This Pat. application claims priority of the Swiss Pat. application No. CH 01067/04 filed on Jun. 24, 2004 as well as of the international application No. PCT/CH2005/000305 filed on May 30, 2005. The entire disclosure of these two applications is incorporated into the present application by explicit reference for all purposes.

RELATED FIELD OF TECHNOLOGY

The present invention relates to a device and a method, for situating pipette or dispenser tips in a system for manipulating liquid samples. Such devices comprise a robot manipulator for orienting pipette or dispenser tips in an X direction and a Y direction, running essentially perpendicularly thereto, in relation to sample containers situated in or on the system. Such devices additionally comprise pipette or dispenser tips which extend essentially vertically and may be raised and lowered in a Z direction running essentially perpendicularly to the X and Y directions. Furthermore, such devices comprise drives for moving a robot manipulator and processors for controlling the movements and actions of the robot manipulator and/or the pipette or dispenser tips.

RELATED PRIOR ART

Corresponding devices and systems are known for use in assaying genes ("genomics"), proteins ("proteomics"), for discovering new active ingredients ("drug discovery"), and in clinical diagnostics ("clinical diagnostics"), such as the work platform distributed under the name "Genesis Robotic Sample Processor" by the applicant. This is a device for manipulating samples in containers and/or on slides, the containers and/or the slides being situated on an essentially horizontal operating field and having a longitudinal dimension X and a transverse dimension Y and the device comprising robot manipulators for manipulating the samples. This manipulation may relate to the aspiration and/or delivery of liquids, e.g., within this X-Y field. In addition, centrifuges and other processing stations or analysis stations for samples may be provided, such as fluorescence readers and the like. The identification of objects, such as sample tubes, microplates, and other containers containing samples using a corresponding device, such as a barcode reader or the like, is also important for such work platforms.

For the purpose of liquid handling, such known work platforms preferably comprise a robot manipulator having an arm extending in the Y direction and at least one rail extending in the X direction, to which the arm is attached so it is movable back and forth in the X direction; pipette tips, which extend essentially vertically and which may be raised and lowered in this Z direction running essentially perpendicularly to the operating field; as well as drives for moving the robot manipulator and processors for controlling the movements and actions of the robot manipulator and/or the pipette tips.

Liquid samples which are to be processed and/or assayed are typically located in tubes or in the wells of microplates. Such tubes are placed in suitable holders, so that each holder may accommodate a series of tubes, which are thus situated neighboring one another in a line in the Y direction, i.e., in the direction of the transverse dimension of the work platforms. These holders are preferably displaceably guided on the work table. Liquid samples may also be located in the wells of microplates, and/or may be pipetted over from the sample tubes into these wells. Three microplates are typically situated on a "carrier", which is preferably also displaceably guided on the work table.

Such work platforms have proven themselves in many regards. However, the necessity often exists of placing the contents of individual tubes or wells of microplates in another container. This may be performed by pipetting over, which becomes cumbersome and time-consuming in particular when, for example, liquid samples must be brought from all wells of four 96-well microplates into the wells of a 384-well microplate.

OBJECT AND SUMMARY OF THE IVENTION

The object of the present invention is to suggest alternative devices and methods, using which the pipetting over of liquid samples in a work platform may be rationalized.

This object is achieved according to the present invention in that a device for situating pipette or dispenser tips in a system for manipulating liquid samples is proposed. This device comprises:
  a robot manipulator for orienting pipette or dispenser tips in an X direction and a Y direction, which runs essentially perpendicularly thereto, in relation to sample containers situated in or on the system;
  pipette or dispenser tips, which extend essentially vertically and may be raised and lowered in a Z direction running essentially perpendicularly to the X and Y direction;
  drives for moving the robot manipulator; and
  processors for controlling the movements and actions of the robot manipulator and/or of the pipette or dispenser tips.

The device according the present invention comprises at least two blocks situated on an arm of the robot manipulator, on each of which at least two pipette or dispenser tips are situated at an axial distance to one another which essentially corresponds to the grid spacing of wells of a microplate, at least one of these blocks—for the alternating interlaced orientation of the pipette or dispenser tips of the two blocks along a shared line—being implemented as individually movable in the X direction and in the Y direction.

This object is achieved according to the present invention in that a method for situating pipette or dispenser tips in a system for manipulating liquid samples having such a device is proposed. This device comprises:
  a robot manipulator for orienting pipette or dispenser tips in an X direction and in a Y direction, which runs essentially perpendicularly thereto, in regard to sample containers situated in or on the system;
  pipette or dispenser tips, which extend essentially vertically and which may be raised and lowered in a Z direction running essentially perpendicularly to the X and Y directions;
  drives for moving the robot manipulator; and
  processors for controlling the movements and actions of the robot manipulator and/or of the pipette or dispenser tips;

The device according the present invention comprises at least two blocks situated on an arm of the robot manipulator, on each of which at least two pipette or dispenser tips are situated at an axial distance to one another which essentially corresponds to the grid spacing of wells of a microplate. The inventive method comprising the step of moving at least one of these blocks individually in the X direction and in the Y direction, so that the pipette or dispenser tips (2) of the two blocks (8,9) are oriented alternately and interlaced along a shared line (12) and assume a first position (I).

Additional features, variations, and improvements according to the present invention result from the dependent claims.

Brief Introduction of the Drawings

Preferred embodiment of the present invention will be explained in greater detail on the basis of schematic figures, without restricting the scope of the present invention thereby.

FIG. 7 shows a partial side view of the pipette or dispenser tips of a device according to the present invention in a first position (I);

FIG. 8 shows a partial side view of the pipette or dispenser tips of a device according to the present invention in a second or third position (II, III).

DETAILED DESCRIPTION OF THE INVENTION

Figure 1:
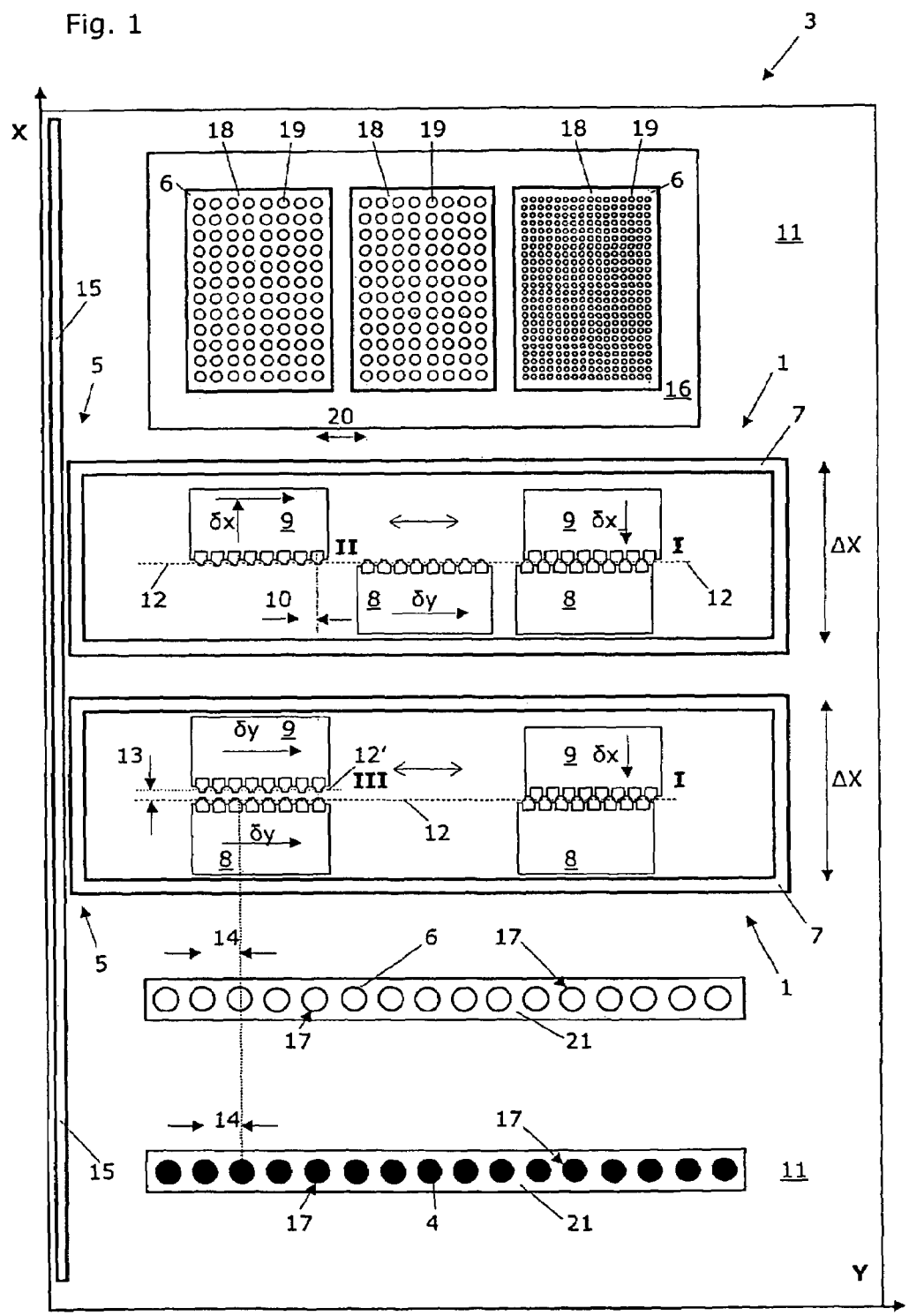
FIG. 1 shows a first schematic overview (top view) of a device according to the present invention, according to a first embodiment having two blocks.

FIG. 1 shows a schematic overview (top view) of a device according to the present invention according to a first embodiment. This device 1 is implemented to situate pipette or dispenser tips 2 (cf. also FIGS. 7 and 8) in a system 3 for manipulating liquid samples 4. The device comprises a robot manipulator 5 for orienting pipette or dispenser tips 2 in an X direction and a Y direction, running essentially perpendicularly thereto, in relation to sample containers 6 situated in or on the system 3.

In connection with the present invention, in the following all possible vessels or substrates for storing liquids are referred to as sample containers 6. These include sample tubes 17 (or "tubes"), microplates 18 and/or their wells (or "wells 19"), reagent bottles and troughs (or "troughs"). Trays having raised or depressed surfaces for receiving samples or even flat surfaces, such as slides (e.g., having arrays of sample situated thereon) or MALDI-TOF targets having droplets deposited thereon may also be viewed as such sample containers 6. Such containers may be used both as a source of liquid samples 4 to be aspirated and also as a target of liquid samples to be delivered. Carriers for samples, which absorb the samples partially or entirely therein, such as membranes or filters, may also be used as such target vessels.

Suitable systems for which the devices according to the present invention may be used comprise the work platform distributed under the name "Genesis Robotic Sample Processor", for example, having a preferably rectangular work table 11. Carriers 16, on which microplates 18 having wells 19, particularly having 96 or 384 wells; and/or racks 21, on which sample tubes 17 may be positioned, have especially proven themselves in these work platforms and/or systems 3. Microplates 18 having other formats, such as 24 or 1536 wells 19, are preferably also used.

The device 1 may also be used in systems 3 having work tables which are round or deviate otherwise from the rectangular shape, if these employ pipette or dispenser tips 2 which extend essentially vertically and may be raised and lowered in a Z direction running essentially perpendicularly to the X and Y directions. The devices according to the present invention additionally comprise drives for moving the robot manipulator 5 and processors for controlling the movements and actions of the robot manipulator 5 and/or the pipette or dispenser tips 2. According to the present invention, the device 1 comprises at least two blocks 8,9 situated on an arm 7 of the robot manipulator 5, on which at least two pipette or dispenser tips 2 are each situated at an axial distance 10 from one another. This axial distance 10 essentially corresponds to the grid spacing of wells 19 of a microplate 18. Devices in which the number of the pipette or dispenser tips 2 per block 8,9 is defined by an integral multiple of the number 2, particularly by the number 4 or 8, are preferred. The axial distance 10 between the pipette or dispenser tips 2 in a block 8,9 is preferably 9 mm or 18 mm.

At least one of these blocks 8,9 of the device 1 according to the present invention is implemented as individually movable in the X direction (shorter arrows) and in the Y direction (longer arrows). This allows an orientation according to the present invention of the pipette or dispenser tips 2 of the two blocks 8,9, in which these pipette or dispenser tips 2 are situated alternately and interlaced along a shared line 12 in a first position (I; cf. FIG. 4). Blocks 8,9 each having 8 pipette or dispenser tips 2 which are situated at an axial distance 10 of 9 mm are especially preferred. Using such a device 1, a series of wells 19 of a 96-well microplate 18 may be processed simultaneously using the pipette or dispenser tips 2 of a single block 8,9. All pipette or dispenser tips 2 may be lowered and/or raised simultaneously. This allows pipette or dispenser tips 2 to be provided which are fixed immovably on this supporting block 8,9, for example. The block 8,9 on the arm 7 of the robot manipulator 5 is implemented so it may be raised and lowered in the Z direction.

Such simple embodiments have the advantage that, per block 8,9, they allow pipetting over of 8 liquid samples 4 from microplates having 96 wells into microplates having 384 wells, or from microplates having 24 wells into microplates having 96 wells (cf. FIG. 1). The reverse path is also possible in each case. However, such blocks 8,9, each having four or eight pipette or dispenser tips 2 mounted fixed thereon at an axial distance of 9 mm or 18 mm, do not allow liquid samples 4 to be aspirated from sample tubes 17 which are not situated at an axial distance 10 from one another which corresponds to the axial distance of the wells 19 of microplates 18. In fact, racks 21 are often used, on which 16 sample tubes are typically situated at an axial distance 14 of 18.8 mm to one another. To remove liquid samples 4 from sample tubes 17, it is either necessary to adapt the axial distance of the sample tubes 17 and the pipette or dispenser tips 2 to one another or to implement the pipette or dispenser tips 2 so they may be lowered and/or raised individually. The parallel transfer of liquid samples from a microplate 24 having 24 wells directly into a microplate having 384 wells (or vice versa) is also otherwise not possible.

Pipette or dispenser tips 2 which are fixed movably on this supporting block 8,9 thus offer greater flexibility, each of the pipette or dispenser tips 2 being implemented so it may be raised and lowered individually in the Z direction. The block 8,9 carrying such individually movable pipette or dispenser tips 2 comprises the suitable drives for lowering and raising the pipette or dispenser tips 2 for this purpose (cf. FIGS. 4 through 6). It is implicitly assumed in the following that the blocks 8,9 are always blocks having such pipette or dispenser tips 2 implemented so they may be raised and lowered individually in the Z direction.

A device 1 according to the present invention preferably comprises two blocks 8,9 (cf. FIG. 1), which are situated mirror reversed to one another. These blocks 8,9 are preferably implemented having essentially identical constructions, so that the production costs may be minimized. A device according to the present invention may also comprise three or four blocks, however (cf. FIG. 3). The blocks 8,9 are partially movable in the X direction (shorter arrows) and in the Y direction (longer arrows).

A system 3 for manipulating liquid samples 4 is shown in the schematic overview of FIG. 1. This system 3 comprises a work table 11 having multiple work fields situated thereon. These work fields are shown here as carriers 16 or racks 21, on which microplates 18 having wells 19 or sample tubes 17 are situated. The sample tubes are situated at an axial distance 14 of 18.8 mm to one another. An alternative design for a rack 21 for sample tubes 17 preferably comprises an axial distance of 18 mm, which precisely corresponds to twice the grid spacing of the wells 19 of a standard microplate. Such an alternative design would be incorporated especially well in the concept of the present invention, because the present invention preferably builds on a grid spacing of the wells of a 96-well standard microplate of 9 mm, and/or a fraction or multiple thereof: two microplates 18 having 96 wells (having a grid spacing of 9 mm) and one microplate 18 having 384 wells 19 (having a grid spacing of 4.5 mm) are shown at the top on the carrier 16.

The robot manipulator 5 comprises a box-shaped arm 7 here, which is mounted on a rail 15 so it is displaceable in the X direction (cf. double arrows ΔX). Two blocks 8,9 are mounted in the box-shaped arm 7 so they are movable in the Y direction. The X direction corresponds to the longitudinal dimension of the work table 11 and the Y direction corresponds to its transverse dimension.

In the upper box-shaped arm 7 (cf. FIG. 1), the two blocks 8,9 are shown in a first position (I: cf. FIG. 4) on the right side. In this position I, the eight pipette or dispenser tips 2 of the first block 8 are situated on a shared line 12 and at an axial distance 10 of 9 mm. The eight pipette or dispenser tips 2 of the second block 9 are also situated on the shared line 12 and at an axial distance 10 of 9 mm. The pipette or dispenser tips 2 of the two blocks 8,9 are arrayed interlaced on the shared line 12, so that a pipette or dispenser tip 2 of the first and second block is always placed alternately on the shared line 12. In this interlaced position I of the pipette or dispenser tips 2, they still have a resulting axial distance of 4.5 mm, which corresponds precisely to the grid spacing of the wells 19 of the microplate 18 having 384 wells situated above. In this interlaced position I of the pipette or dispenser tips 2, all 16 wells of a row in such a 384-well microplate may thus be reached exactly and simultaneously in one action using the pipette or dispenser tips 2. It is thus possible to aspirate 16 fluid samples 4 from the wells 19 of a row simultaneously and dispense them again simultaneously in a row of wells 19 of the same or another 384-well microplate 18 (not shown). The blocks 8,9 may remain in their interlaced position I during the movement between aspiration and dispensing.

The two blocks 8,9 are shown in a second position (II; cf. FIG. 5) in the upper box-shaped arm 7 (cf. FIG. 1) on the left side. In this position II, the eight pipette or dispenser tips 2 of the first block 8 are situated on a shared line 12 and at an axial distance 10 of 9 mm. The eight pipette or dispenser tips 2 of the second block 9 are also situated on the shared line 12 and at an axial distance 10 of 9 mm. The pipette or dispenser tips 2 of the two blocks 8,9 are arrayed neighboring one another on the shared line 12, so that they are separated from one another by an intermediate space 20. In this position II of the pipette or dispenser tips 2, they have the intrinsic axial distance of 9 mm, which precisely corresponds to the grid spacing of the wells 19 of the microplate 18 having 96 wells situated above. In this position II of the pipette or dispenser tips 2, all 8 wells in a row of such a 96-well microplate may thus be reached exactly and simultaneously in one action by the pipette or dispenser tips 2. It is thus possible to aspirate 16 liquid samples 4 from each of the eight wells 19 of a row of two neighboring 96-well microplates and dispense them again simultaneously in a row of wells 19 of the same or two other 96-well microplates 18. The blocks 8,9 may remain in their position II during the movement between aspiration and dispensing.

If a change from the position I (right) to the position II (left) is completed by the two blocks 8,9 between the aspiration and the dispensing, 16 liquid samples 4 from the wells 19 of a row in a 384-well microplate may be aspirated simultaneously in one action and delivered simultaneously in each of the eight wells 19 of a row of two neighboring 96-well microplates. During this dispensing, the pipette or dispenser tips 2 of the two blocks 8,9 are arrayed neighboring one another on a shared line 12, so that they are separated from one another by an intermediate space 20. The dimensions for this intermediate space 20 expediently depend on the distance of the closest well columns of two neighboring microplates 18 on a carrier 16. This distance may be 25 mm or 30 mm, for example.

If a change from the position II (left) to the position I (right) is completed by the two blocks 8,9 between aspiration and dispensing, 16 liquid samples 4 may be aspirated simultaneously from each of the eight wells 19 of one row of two neighboring 96-well microplates 18 and delivered simultaneously into the 16 wells 19 of a row in a 384-well microplate in one action.

The two blocks 8,9 are again shown in a first position (I; cf. FIG. 4) in the lower box-shaped arm 7 (cf. FIG. 1) on the right side. On the left side, the two blocks 8,9 are situated here in the third position (III; cf. FIG. 6). In this position III, the eight pipette or dispenser tips 2 of the first block 8 are situated on a shared line 12 and at an axial distance 10 of 9 mm. The eight pipette or dispenser tips 2 of the second block 9 are situated on a parallel line 12' and at an axial distance 10 of 9 mm. The pipette or dispenser tips 2 of the second block 9 are precisely opposite the pipette or dispenser tips 2 of the first block 8. In this position III of the pipette or dispenser tips 2, they have their intrinsic axial distance of 9 mm, which precisely corresponds to the grid spacing of the wells 19 of the microplate 18 having 96 wells situated above. In addition, the two lines 12, 12' are separated from one another by precisely the grid spacing of 9 mm. In this position III of the pipette or dispenser tips 2, all 16 wells of two neighboring rows of such a 96-well microplate may thus be reached exactly and simultaneously by the pipette or dispenser tips 2 in one action. It is thus possible to aspirate 16 liquid samples 4 from the eight wells 19 of each one of these two rows and dispense them again simultaneously in a double row of wells 19 of the same or another 96-well microplate 18. The blocks 8, 9 may remain in their position III during the movement between aspiration and dispensing.

If a change from the position I (right) to the position III (left) is now completed by the two blocks 8,9 between the aspiration and the dispensing, 16 liquid samples 4 from the wells 19 of a row in a 384-well microplate may be aspirated simultaneously in one action and delivered simultaneously into each of the eight wells 19 of two neighboring rows of a 96-well microplate. During this dispensing, the pipette or dispenser tips 2 of the two blocks 8,9 are arrayed opposite one another on a shared line 12 or on a parallel line 12', so that they are separated from one another by distance 13. The dimensions for this distance 13 expediently depend on the grid spacing of the wells 19 of a microplate 18 on a carrier 16. This distance is preferably 9 mm, but may also be 18 mm.

If a change from the position III (left) to the position I (right) is completed by the two blocks 8,9 between aspiration and dispensing, 16 liquid samples 4 may thus be aspirated simultaneously from each of the eight wells 19 of two neighboring rows on a 96-well microplate 18 and delivered simultaneously into the 16 wells 19 of a row in a 384-well microplate in one action.

A liquid handling system 3, in which the blocks 8,9 of the device 1 having the pipette or dispenser tips 2 are movable back and forth essentially in the entire area of the work table 11 in the X direction and in the Y direction, is especially preferred. As shown on the bottom of FIG. 1, racks 21 may also be situated on the work table 11, which are capable of carrying sample tubes 17. As already noted, the pipette or dispenser tips 2 may be raised or lowered as needed, so that liquid samples 4 may be taken from the sample tubes 17 or delivered therein. The individual movements of the blocks 8, 9 within the box-shaped arm 7 of the robot manipulator 5 are indicated by solid arrows and identified by $\delta x$ and/or $\delta y$.

Figure 2:
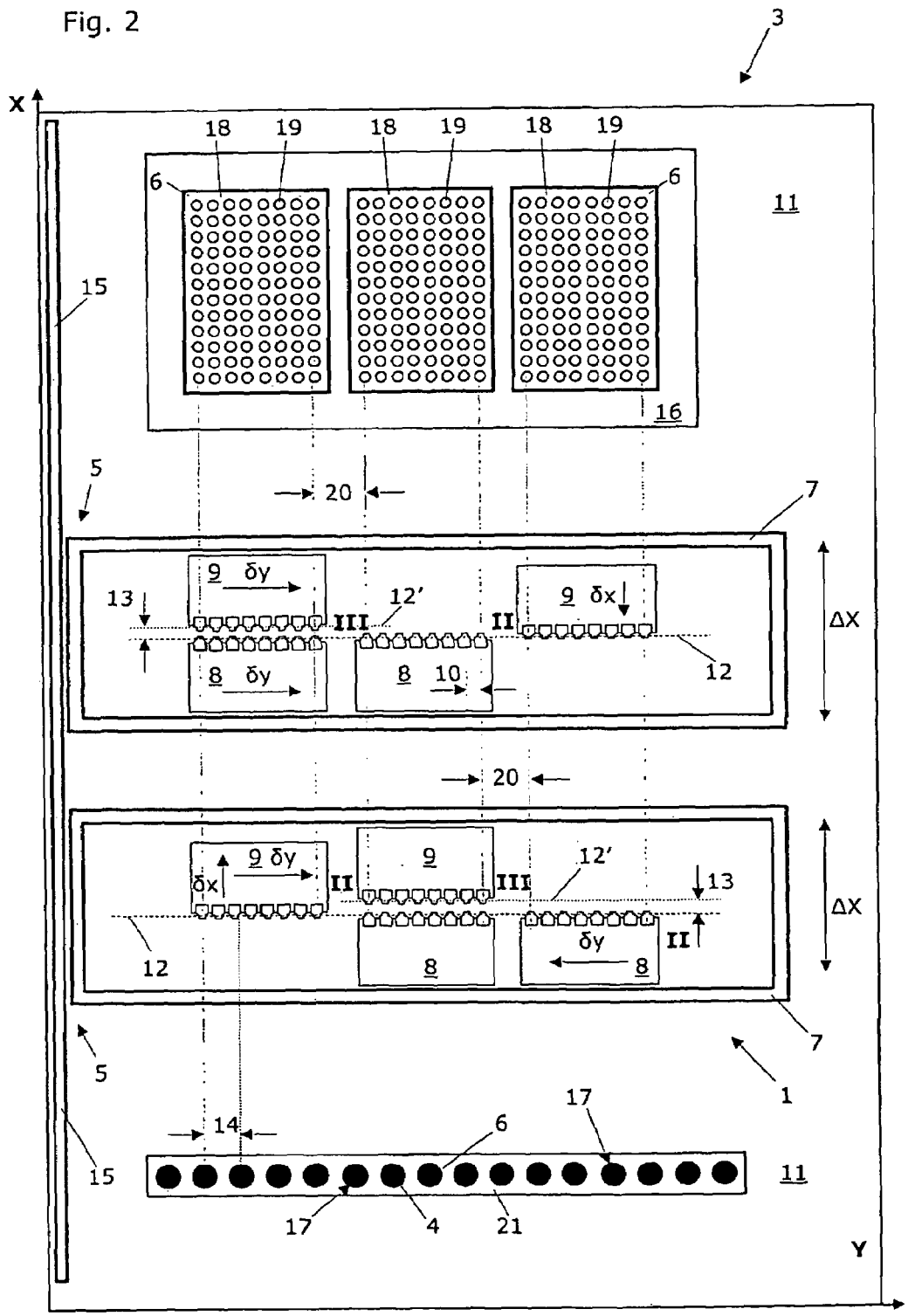
FIG. 2 shows a further schematic overview (top view) of a device according to the present invention, according to the first embodiment having two blocks.

FIG. 2 shows a further schematic overview (top view) of a device according to the present invention, according to the first embodiment having two blocks. The carrier 16 having three 96-well microplates and/or a 16-position rack 21 for sample tubes 17 is placed on the work table 11. Two variations of the arrangement of two blocks 8,9 having pipette or dispenser tips 2 are shown between them. The blocks 8,9 are partially movable in the X direction (shorter arrows) and in the Y direction (longer arrows). The individual movements of the blocks 8, 9 within the box-shaped arm 7 of the robot manipulator 5 are indicated by solid arrows and identified by $\delta x$ and/or $\delta y$.

The two blocks 8,9 are again situated in the third position III (cf. FIG. 6) in the upper box-shaped arm 7 on the left side. The two blocks 8,9 are situated in a second position (II) in the middle and on the right side here. If a change from the position III (left) to the position II (right) is completed by the two blocks 8,9 between aspiration and the dispensing, 16 liquid samples 4 may be aspirated simultaneously from the eight wells 19 of each of two neighboring rows on a 96-well microplate 18 and delivered simultaneously into the 8 wells 19 of one row each of two neighboring 96-well microplates 18 in one action. Samples from 16 wells of a microplate may thus be distributed simultaneously to two microplates of the same dimensions. In the reverse direction, there is a collection of 2×8 samples of two microplates into 16 wells of a single microplate of the same size.

The two blocks 8,9 are again situated in the third position III and in the second position II in the lower box-shaped arm 7. If a change from the position II (left and right) to the position III (middle) is completed by the two blocks 8,9 between aspiration and the dispensing, 16 liquid samples 4 may be aspirated simultaneously from the eight wells 19 of each corresponding row of two 96-well microplates 18 distal from one another and delivered simultaneously into the two neighboring rows of wells 19 of a microplate 18 preferably lying in between in one action. Samples from 16 wells of two microplates may thus be collected simultaneously on two 8-well rows of wells 19 of a microplate of the same dimensions. In the reverse direction, 2×8 liquid samples of a single microplate 16 are distributed into 16 wells of two microplates 18 of the same size. In contrast to the above exemplary embodiment, the example shown here has the advantage that the travel paths of the blocks 8,9 are practically of identical length, so that a time savings results.

Furthermore, a rack 21 is used, on which the preferably 16 sample tubes 17 are situated at an axial distance 14 of 18.8 mm to one another. The pipette or dispenser tips 2 are lowered individually to remove liquid samples 4 from the sample tubes 17. The pipette or dispenser tips 2 are lowered individually to dispense liquid samples 4 into the sample tubes 17. The pipette or dispenser tips 2 which are not in register with the sample tubes are raised additionally as needed so that collisions are prevented.

Figure 3:
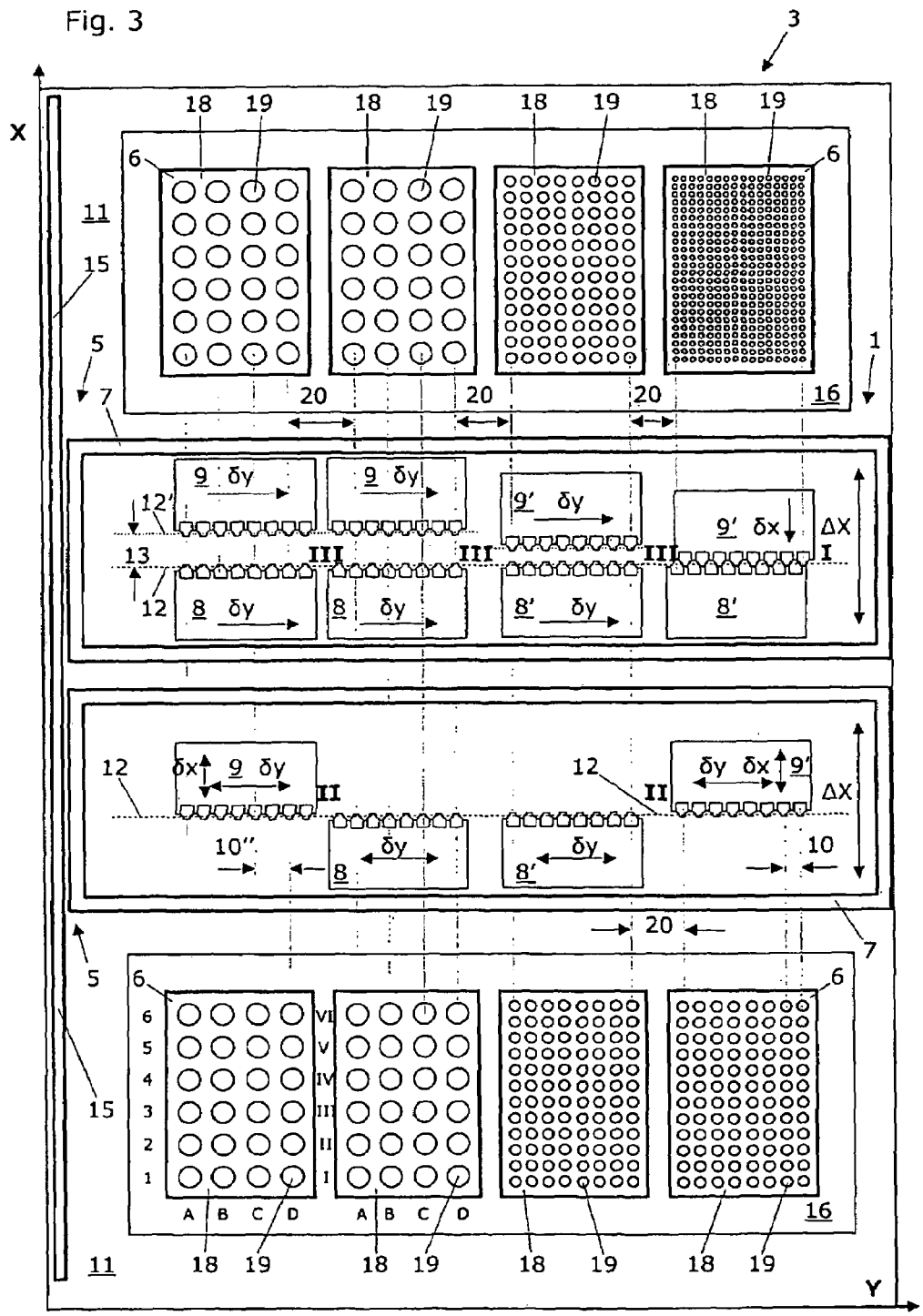
FIG. 3 shows a schematic overview (top view) of a device according to the present invention, according to a second embodiment having four blocks.

FIG. 3 shows a schematic overview (top view) of a device according to the present invention, according to a second embodiment having four blocks 8,8',9,9'. A carrier 16 having four microplates 18 is deposited on the work table 11. The upper carrier 16 carries two microplates 18 having 24 wells 19 and a microplate 18 having 96 or 384 wells. The lower carrier 16 carries two microplates 18 having 24 or 96 wells 19. Two exemplary embodiments are indicated between them. As in FIGS. 1 and 2, it does not mean here that the system 3 must comprise a robot manipulator 5 having two arms 7. Although this is not excluded, situating only one arm 7 having two or four blocks 8,8',9,9' is preferred, because one such arm 7 may serve the entire work table 11, without a collision with a second arm 7 or at least an obstruction by this arm to be feared.

The two blocks 8,9 are again situated in the third position III (cf. FIG. 6) in the upper box-shaped arm 7 on the left side. The distance 13 is 18 mm here—corresponding to the grid spacing of the wells 19 of the 24-well microplates. This dimension corresponds to double the axial distance of the pipette or dispenser tips 2 on the blocks 8,9. Therefore, to pipette over between the 24-well microplates, only the even-numbered or odd-numbered pipette or dispenser tips 2 may always be used simultaneously. This exemplary embodiment also illustrates, however, that it is possible thanks to the device 1 according to the present invention to perform a sample concentration directly from 24-well microplates into the wells of a 384-well microplate (or if needed with an intermediate step in a 96-well microplate). If four blocks 8,8',9,9' are used, pipetting over may be performed into the two 24-well microplates and simultaneously from the 384-well microplate into the 96-well microplate. In addition, "hit-picking" may also be performed, in that only the contents of a selected number or selected positions of wells in all or selected formats are processed. The individual movements of the blocks 8,8',9,9' within the box-shaped arm 7 of the robot manipulator 5 are indicated by solid arrows and identified by $\delta x$ and/or $\delta y$.

It will be immediately clear to those skilled in the art upon reading the present description that the present invention offers a large palette of possibilities for pipetting over, which are all included by the idea of the present invention. The consolidation of samples—starting from two 24-well microplates and leading to a 96-well microplate—is to be described here as a representative and in no way exhaustive possibility. A system 3 having two blocks 8,9, in each of which 8 pipette tips 2 are inserted at a distance of 9 mm to one another, is used as an instrument for performing the pipetting over. A similar configuration is shown in FIG. 3 (bottom), only one of the two 96-well microplates shown being charged, however. The pipetting over is performed in the following steps:

Aspiration 1:

A setting of the blocks corresponding to position II is preferably selected, so that all pipette tips 2 are situated on a shared line 12. The arm 7 of the robot manipulator is moved far enough in the X direction that this imaginary line 12 runs centrally through the first row of the wells 19. Preferably, as indicated by the thin lines which run from the pipette tips 2 to the wells 19 (cf. FIG. 3 bottom), in block 9, only the pipette tips 2 having an odd number (1,3,5,7) and in block 8, only the pipette tips 2 having an even number (2,4,6,8) are selected for the imminent aspiration, for example. An axial distance 10" between the pipette tips 2 of 18 mm is thus defined, which precisely corresponds to the grid spacing of the wells of the sighted 24-well microplate. The two blocks 8,9 must still be moved far enough in the Y direction so that the selected pipette tips 2 are above the center of the corresponding wells 19. The selected pipette tips 2 are then lowered into the first row of wells 19 of the two microplates 18 having 24 wells 19.

A specific first quantity of liquid from each well 19 of the first two rows of the 24-well microplates is sucked into the pipette tips 2 lowered below the liquid level in the wells 19 and the pipette tips 2 having aspirated liquid samples are then raised.

Aspiration 2:

All pipette tips 2 remain situated on a shared line 12. The setting of the blocks 8,9 according to position II is only changed enough that the intermediate space 20 between the blocks 8,9 is adapted to the pipette tips 2 now to be lowered. For this purpose, the blocks 8,9 are moved accordingly in the Y direction. The arm 7 of the robot manipulator is moved far enough in the X direction that this imaginary line 12 runs centrally through the second row of the wells 19. In block 9, only the pipette tips 2 having an even number (2,4,6,8) and in block 8 only the pipette tips 2 having an odd number (1,3,5,7) are then selected for the imminent aspiration. An axial distance 10" between the pipette tips 2 of 18 mm is thus again defined, which corresponds precisely to the grid spacing of the wells of the intended 24-well microplates. The selected pipette tips 2 of the two blocks 8,9 are now above the center of the corresponding wells 19. The selected pipette tips 2 are then lowered into the second row of wells 19 of the two microplates 18 having 24 wells 19.

A specific first quantity of liquid from each well 19 of the two second rows of the 24-well microplates is sucked into the pipette tips 2, which are lowered below the liquid level in the wells 19, and the pipette tips 2 having the aspirated liquid samples are then raised.

All 16 pipette tips of the two blocks 8,9 now contain a specific first quantity of an aspirated liquid sample. The samples originate from the two microplates as may be seen from following Table 1. In this example, the rows of the wells of the left microplate are numbered using Arabic numbers and the rows of the wells of the right microplate are numbered using Roman numbers. The wells of each row are identified from the left beginning in each case with a letter A-D (cf. FIG. 3).

TABLE 1

Arrangement of the aspirated samples in the blocks

| Block 9 Pipette tips | | | | | | | | Block 8 Pipette tips | | | | | | | |
|---|---|---|---|---|---|---|---|---|---|---|---|---|---|---|---|
| 1 | 2 | 3 | 4 | 5 | 6 | 7 | 8 | 1 | 2 | 3 | 4 | 5 | 6 | 7 | 8 |
| | | | Samples | | | | | | | | Samples | | | | |
| 1A | 2A | 1B | 2B | 1C | 2C | 1D | 2D | IIA | IA | IIB | IB | IIC | IC | IID | ID |

Transfer:

All pipette tips 2 are now situated on two lines 12,12', corresponding to position III. The setting of the blocks 8,9 according to position III is altered so that the pipette tips 2 of the two blocks 8,9 are exactly opposite, and the two lines 12,12' are spaced apart from one another by the axial distance 10 of the pipette tips 2 of 9 mm. For this purpose, the blocks 8,9 are moved accordingly in the Y direction. In addition, at least one of the blocks 8,9 must also be moved in the X direction to achieve a relative distance of 9 mm. The arm 7 of the robot manipulator 5 is moved far enough in the X direction that this imaginary line 12 or 12', respectively, runs centrally through the first or second row of the wells 19 of the intended 96-well microplate 18. In addition, the two blocks 8,9 are moved as a unit in the Y direction, until all pipette tips are over the center of the corresponding wells 19 of the 96-well microplate. All pipette tips 2 are then lowered simultaneously into the first or second row of wells 19 of the microplate 18 having 96 wells 19.

Dispensing:

A specific second quantity of liquid is dispensed from each pipette tip 2 into a well 19 of the first and second rows of the 96-well microplate 18, e.g., from the air or with contact of the surface of the well 19 or a liquid already present therein. The first and second quantities of the liquid samples may be identical (single consolidation into a 96-well microplate) or may have different volumes (multiple consolidation into multiple 96-well microplates 18).

The pipette tips 2 are then raised and, if they are no longer necessary, are discarded in a waste container or cleaned. This pipetting over procedure is repeated twice more (if necessary, using fresh disposable pipette tips in each case or using flushed and cleaned steel tips), so that samples from all wells 19 of the two 24-well microplates are transferred to the 96-well microplate. If desired, corresponding samples may be transferred from two further 24-well microplates 18 to the 96-well microplate (not shown).

All 2×24 samples transferred to a 96-well microplate in this way are situated as shown in Table 2 in this example.

TABLE 2

Arrangement of the dispensed samples in the 96-well microplate

| | Column | | | | | | | |
|---|---|---|---|---|---|---|---|---|
| Row | A | B | C | D | E | F | G | H |
| 12 | | | | | | | | |
| 11 | | | | | | | | |

TABLE 2-continued

Arrangement of the dispensed samples in the 96-well microplate

| Row | Column | | | | | | | |
|---|---|---|---|---|---|---|---|---|
| | A | B | C | D | E | F | G | H |
| 10 | | | | | | | | |
| 9 | | | | | | | | |
| 8 | | | | | | | | |
| 7 | | | | | | | | |
| 6 | 5A | 6A | 5B | 6B | 5C | 6C | 5D | 6D |
| 5 | VIA | VA | VIB | VB | VIC | VC | VID | VD |
| 4 | 3A | 4A | 3B | 4B | 3C | 4C | 3D | 4D |
| 3 | IVA | IIIA | IVB | IIIB | IVC | IIIC | IVD | IIID |
| 2 | 1A | 2A | 1B | 2B | 1C | 2C | 1D | 2D |
| 1 | IIA | IA | IIB | IB | IIC | IC | IID | ID |

If the blocks are situated alternatively, so that in the first aspiration step pipette tips 2 having odd numbers are used in block 8 and those having even numbers are used in block 9, a different arrangement of the samples in the 96-well microplate thus correspondingly results. The mutual setting of the blocks 8 and 9 in position II may also be switched. Furthermore, the aspiration may occur in that the blocks 8, 9 are in position III instead of in position II. Independently of which variation is selected, the path of each sample from the starting position in the 24-well microplate up to the final position in the 96-well microplate may be tracked logically and uniquely. This statement also applies for the reverse operation, of course, if samples from a 96-well microplate are to be distributed into two or four 24-well microplates.

This example may be transferred essentially to all possible types of pipetting over, in which arbitrary containers, such as sample tubes and microplates, as well as arbitrary configurations of the blocks 8,9 in the positions I, II, or III are used. The travel paths of the blocks 8,9 may be kept very small thanks to the device 1 according to the present invention and 16 samples may be dispensed simultaneously into the 96-well microplate in each case or aspirated from such a microplate. A time saving for the action of pipetting over thus results in relation to systems such as those known from the prior art.

In the lower box-shaped arm 7, the four blocks 8,8',9,9' are situated in pairs in the second position II. In this arrangement—as shown in the example of 24-well and 96-well microplates—efficient dispensing of liquid samples 4 into different microplate formats may also be performed.

Figure 4:
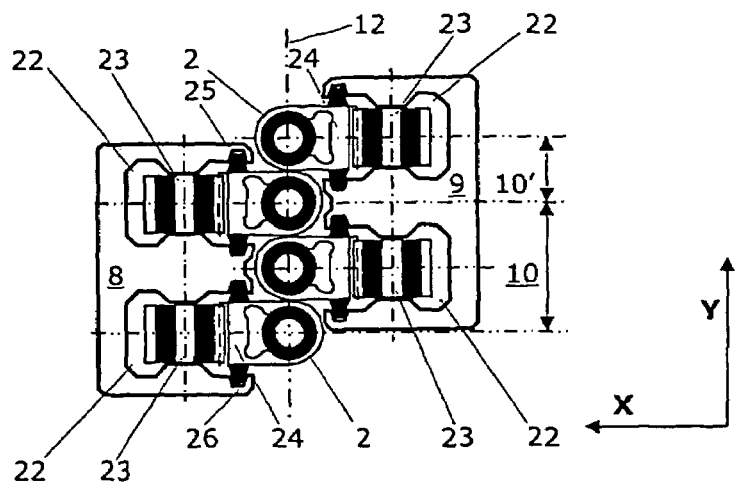
FIG. 4 shows a schematic horizontal section through two blocks of a device according to the present invention, in a first position (I)

FIG. 4 shows a schematic horizontal section through two blocks 8,9 of a device 1 according to the present invention, in a first position (I). In this position I, all pipette or dispenser tips 2 of the first block 8 are situated on a shared line 12 and at an axial distance 10 which corresponds exactly to the grid spacing of the wells 19 of a microplate 18. The axial distance 10 is preferably 9 mm (corresponding to the grid spacing of a 96-well microplate), but it may also be 18 mm (corresponding to the grid spacing of a 24-well microplate) or another suitable dimension. The pipette or dispenser tips 2 of the second block 9 are also situated on the shared line 12 and at the identical axial distance 10. The pipette or dispenser tips 2 of the two blocks 8,9 are arrayed interlaced on the shared line 12, so that a pipette or dispenser tip 2 of the first and second blocks is always situated alternately on the shared line 12. In this interlaced position I of the pipette or dispenser tips 2, they still have a resulting axial distance 1', which corresponds precisely to half the grid spacing of the wells 19 of a microplate 18. For the sake of simplicity, the blocks 8,9 are each shown here having only two pipette or dispenser tips 2. However, each of these blocks 8,9 preferably comprises 8 pipette or dispenser tips 2.

Each block 8,9 has cage structures 22. Each of these cage structures 22 comprises a pinion 23 which engages in the teeth of a toothed rack 24. The toothed racks 24 of a block 8,9 are situated neighboring at the same axial distance 10 as the pipette or dispenser tips 2 and extend in the Z direction. One of these pipette or dispenser tips 2 is attached to each toothed rack 24 and thus implemented as movable individually in the Z direction, running essentially perpendicularly to the worktable 11. The drives for the pinions 23 are preferably located on each block 8,9.

The toothed racks 24 are implemented as movable over a Z travel path, in that they are each engaged with a pinion 23 of a Z drive (not shown), which is individually driven by a motor and preferably exerts a contact pressure on the particular toothed rack 24. The toothed racks 24 comprise two Z rails 25 projecting laterally in the Y direction and extending in the Z direction, which are mounted to slide in Z guides 26 of an assigned cage structure 22 supporting the individual pinion 23. In the position I shown, the toothed racks 24 are situated alternately together with the particular assigned cage structure 22 of the blocks 8,9 neighboring one another along the shared line 12 extending in the Y direction so that the cage structures 22 lie alternately in front of or behind the shared line 12.

Figure 5:
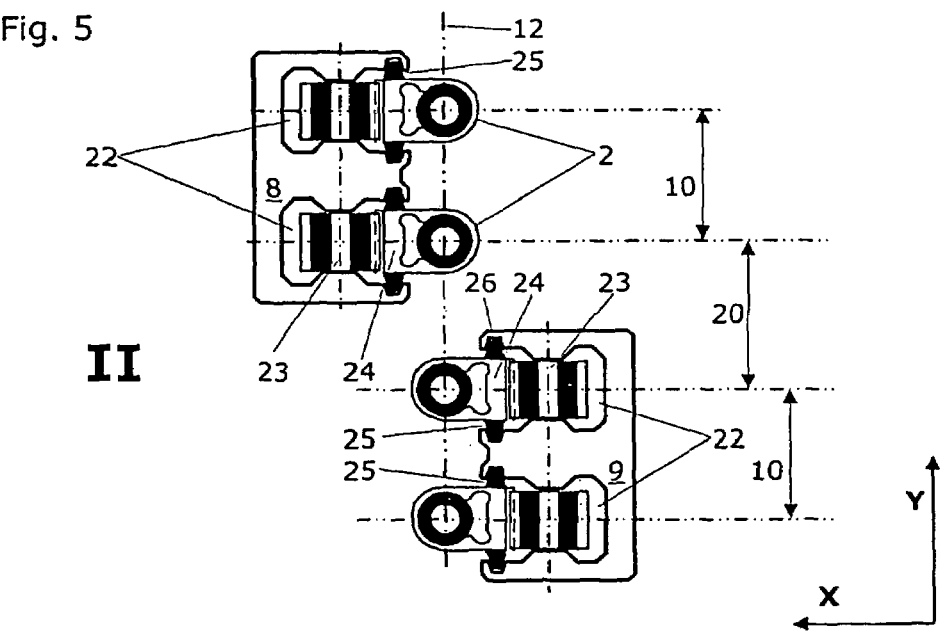
FIG. 5 shows a schematic horizontal section through two blocks of a device according to the present invention, in a second position (II)

FIG. 5 shows a schematic horizontal section through two blocks 8,9 of a device 1 according to the present invention, in a second position (II). In this position II, all pipette or dispenser tips 2 of the first block 8 are situated on a shared line 12 and at an axial distance 10 which preferably precisely corresponds to the grid spacing of the wells 19 of a microplate 18. The axial distance 10 is preferably 9 mm (corresponding to the grid spacing of a 96-well microplate), but it may also be 18 mm (corresponding to the grid spacing of a 24-well microplate) or another suitable dimension. The pipette or dispenser tips 2 of the second block 9 are also situated on the shared line 12 and at the same axial distance 10. The pipette or dispenser tips 2 of the two blocks 8,9 are arrayed neighboring on the shared line 12, so that they are separated from one another by an intermediate space 20 (cf. also FIG. 1).

The two blocks 8, 9 are preferably constructed mirror symmetrically and were already described with reference to FIG. 4 in connection with the cage structures 22, the pinions 23, the toothed racks 24, the Z rails 25, and the Z guides 26. In position II shown, the toothed racks 24 are arrayed together with the particular assigned cage structure 22 of the blocks 8,9 neighboring one another along the shared line 12 extending in the Y direction in such a way that the last cage structure 22 of the block 8 is separated by an intermediate space 20 (cf. also FIG. 1) from the first cage structure 22 of the block 9.

Figure 6:
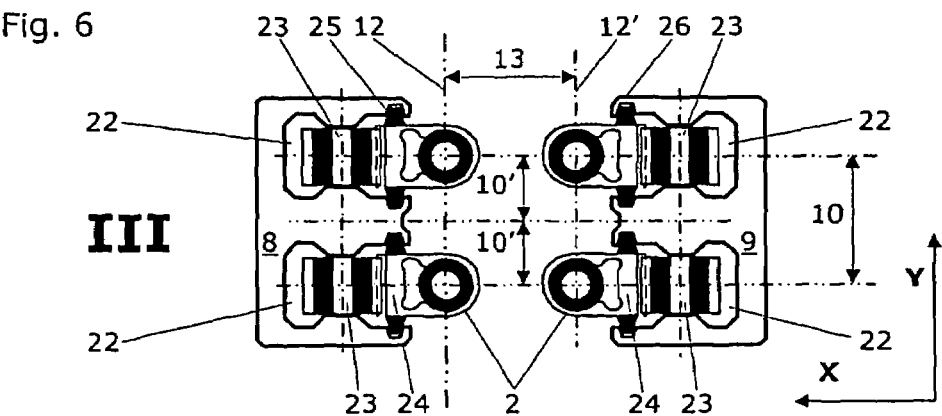
FIG. 6 shows a schematic horizontal section through two blocks of a device according to the present invention, in a third position (III)

FIG. 6 shows a schematic horizontal section through two blocks 8,9 of a device 1 according to the present invention as shown in FIG. 4 or 5, but in a third position (III). In this position III, all pipette or dispenser tips 2 of the first block 8 are situated on a shared line 12 and at an axial distance 10 which preferably corresponds precisely to the grid spacing of the wells 19 of a microplate 18. The axial spacing 10 is preferably 9 mm (corresponding to the grid spacing of a 96-well microplate), but it may also be 18 mm (corresponding to the grid spacing of a 24-well microplate) or another suitable dimension. The pipette or dispenser tips 2 of the second blocks 9 are situated opposite the pipette or dispenser tips 2 of the first block 8 on the parallel line 12' and at the same axial distance 10.

FIG. 7 shows a partial side view of the pipette or dispenser tips 2 of a device 1 according to the present invention in a first position (I). The holders 27 of the pipette or dispenser tips 2 of the first block 8 are marked by a cross. The pipette or dispenser tips 2 of the first and second blocks 8,9 are situated at an axial distance 10 to one another. This axial distance 10 is 9 mm here. The halved axial distance resulting from the interlaced position I of the pipette or dispenser tips 2 is accordingly 4.5 mm. All pipette or dispenser tips 2 of the two blocks 8,9 are lowered and plunged into the wells 19 of a microplate 18 having 384-wells. FIG. 7 shows an exemplary situation after the dispensing of a liquid sample 4 into each of the wells 19. A detail from a 1536-well microplate is shown underneath this. The axes 28 of the pipette or dispenser tips 2 shown are incident in each well 19 of a row in the 384-well microplate (identified by 384). In contrast, only every second well 19 of the microplate (identified by 1536) having the highest density of 1536 wells 19 is hit.

FIG. 8 shows a partial side view of the pipette or dispenser tips 2 of a device 1 according to the present invention in a second or third position (II, III). The holders 27 of the pipette or dispenser tips 2 of the first block 8 are marked by a cross. The pipette or dispenser tips 2 of the second blocks 9 are remote from the position I (dotted, not lowered) and situated either next to or behind the pipette or dispenser tips 2 according to the second position II or the third position III (not shown). The axial distance 10 is also 9 mm here. If only every second pipette or dispenser tip 2 of the first block 8 is lowered, the lowered tips (shown in solid lines) plunge into the wells 19 of a micro plate 18 having 24 wells. Each of the neighboring tips (shown by dashed lines) may not be lowered or must even be raised so that they do not collide with the surface of the microplate 18 (identified by 24). FIG. 8 shows an exemplary situation during the aspiration of a liquid sample 4 from each of the wells 19 of a 24-well microplate. A detail from a 96-well microplate is shown underneath this. The axes 28 of the pipette or dispenser tips 2 shown are incident in each well 19 of a row in this 96-well microplate (identified by 96), so that all pipette or dispenser tips 2 of a block 8,9 may be lowered to process such a microplate. This is with the condition, of course, that the axial distance 10 is 9 mm.

As already described above, individual pipette or dispenser tips 2 may be lowered arbitrarily and individually, so that liquid samples 4 may be aspirated from sample tubes 17, from specific, individual wells 19 of a microplate 18, or from microplates 18 which have a grid constant of the well configuration which does not correspond to the axial distance 10 of the pipette or dispenser tips 2 of the device 1 according to the present invention.

The method according to the present invention for situating pipette or dispenser tips 2 in a system 3 for manipulating liquid samples 4 comprises the use of at least one device 1 just described. The method according to the present invention is characterized in that the device 1 comprises at least two blocks 8,9 situated on an arm 7 of a robot manipulator 5, on which at least two pipette or dispenser tips 2 are situated at an axial distance 10 to one another, this axial distance 10 essentially corresponding to the grid spacing of wells 19 of a microplate 18. At least one of these blocks 8,9 is moved individually in the X direction and in the Y direction, so that the pipette or dispenser tips 2 of the two blocks 8,9 are oriented alternately and interlaced along a shared line 12 and assume a first position (I). In addition, two blocks 8,9 are situated neighboring one another and having an intermediate space 20 to one another by the method according to the present invention, so that the pipette or dispenser tips 2 are situated along the shared line 12 and assume a second position (II). Moreover, the blocks 8,9 are situated opposite one another practically mirror symmetrically at a distance 13 by the method according to the present invention, so that the pipette or dispenser tips 2 are opposite in two spaced lines 12' and assume a third position (III).

By regrouping the blocks 8,9 having the pipette or dispenser tips 2—starting from the first position I and leading to the second position II or the third position III—pipetting over and distributing of the liquid samples 4 from a 384-well microplate to 96-well microplates may be performed.

By regrouping the blocks 8,9 having the pipette or dispenser tips 2—starting from the second position II or the third position III and leading to the first position I—pipetting over and consolidation of the liquid samples 4 from 96-well microplates 18 to a 384-well microplate 18 may be performed.

Without regrouping the blocks 8,9 having the pipette or dispenser tips 2—while maintaining the first position I, the second position II, or the third position III—pipetting over of the liquid samples 4 from arbitrary microplates 18 into microplates having identical size and/or having identical format may be performed. Therefore, the contents of microplates 18 may be copied or replicated in a timesaving way by 16 pipette or dispenser tips 2 which are preferably used simultaneously.

By individually lowering the pipette or dispenser tips 2—starting from the first, second, or third position and leading to the first position I—pipetting over of the liquid samples 4 from sample tubes 17 or from 24-well microplates into a 96-well or a 384-well microplate 18 may be performed.

By individually lowering the pipette or dispenser tips 2—starting from the first position I and leading to the first, second, or third position—pipetting over of the liquid samples 4 from a 96-well or a 384-well microplate 18 into sample tubes 17 or into 24-well microplates may be performed.

For specific operations, pipetting and/or dispensing, on 24-well microplates or racks 21 having sample tubes 17, it may be advantageous for the lowering of non-selected pipette or dispenser tips 2 not to be dispensed with, but rather the spaces in the blocks 8,9 not intended for the work not to be equipped with pipette or dispenser tips 2 at all.

All examples and remarks made on the aspiration and dispensing of liquid samples 4 (pipetting) also apply accordingly for the simple dispensing of such samples (dispensing). The reference numerals in the figures each refer to corresponding parts of the device, even if reference was not made thereto in greater detail in the description. Expedient combinations of the exemplary embodiments shown and/or described are included in the scope of the present invention.

The invention claimed is:

1. A device for situating pipette tips in a system for manipulating liquid samples, this device comprising:

A robot manipulator for orienting pipette or dispenser tips in an X direction and in a Y direction, which runs essentially in a Z direction perpendicularly to the X and Y direction; in relation to sample containers situated in or on the system;

Pipette or dispenser tips, which extend essentially vertically and may be raised and lowered in the Z direction running essentially perpendicularly to the X and Y direction;

Drives for moving the robot manipulator; and

Processors for controlling the movement and actions of the robot manipulator and/or of the pipette or dispenser tips;

Wherein the device comprised at least two blocks situated on an arm of the robot manipulator, on each of which at least two of said pipette or dispenser tips are situated at an axial distance to one another which essentially corresponds to the grid spacing of wells of a microplate, at least one of these blocks—for the alternating interlaced orientation of the pipette or dispenser tips of the two blocks along a shared line—being implemented as individually movable in the X direction and in the Y direction.

2. The device according to claim 1, wherein the pipette or dispenser tips are fixed immovably on the block supporting them, the block being implemented so it may be raised and lowered in the Z direction.

3. The device according to claim 1, wherein the pipette or dispenser tips are fixed movably on the block supporting them, each of the pipette or dispenser tips being implemented so it may be raised and lowered individually in the Z direction.

4. The device according to claim 1, wherein each two of the blocks are implemented having essentially identical constructions and are situated mirror-reversed to on another.

5. The device according to claim 4, wherein the blocks may be situated neighboring one another and having an intermediate space to one another, so that the pipette or dispenser tips are situated along the shared line.

6. The device according to claim 4, wherein the blocks may be situated mirror symmetrically opposite one another at a distance, so that the pipette or dispenser tips are opposite one another in two spaced lines.

7. The device according to claim 1, wherein the number of the pipette or dispenser tips per block is defined by an integral multiple of the number 2, or by the number 4 or 8.

8. The device according to claim 1, wherein the axial distance between the pipette or dispenser tips in a block is 4.5 mm, 9 mm, or 18 mm.

9. A system for manipulating liquid samples having at least one essentially horizontal work field and sample containers which may be situated thereon, comprises at least one device for situating pipette or dispenser tips according to claim 1.

10. The system according to claim 9, wherein the blocks of the device having the pipette or dispenser tips are movable back and forth in the X direction and in the Y direction in essentially the entire area of the work table.

11. The system according to claim 10, comprising at least one carrier or one rack, on which microplates having wells or sample tubes are positioned.

12. A method for situating pipette or dispenser tips in a system for manipulating liquid samples having a device, which comprises:

A robot manipulator for orienting pipette or dispenser tips in an X direction and in a Y direction, which runs essentially in a Z direction perpendicularly to the X and Y direction; in relation to sample containers situated in or on the system;

Pipette or dispenser tips, which extend essentially vertically and may be raised and lowered in the Z direction running essentially perpendicularly to the X and Y directions;

Drives for moving the robot manipulator; and

Processors for controlling the movements and actions of the robot manipulator and/or of the pipette or dispenser tips;

Wherein the device comprises at least two blocks situated on an arm of the robot manipulator, on each of which at least two of said pipette or dispenser tips are situated at an axial distance to one another which essentially corresponds to the grid spacing of wells of a microplate, at least one of these blocks—for the alternating interlaced orientation of the pipette or dispenser tips of the two blocks along a shared line—being implemented as individually movable in the X direction and in the Y direction.

13. The method according to claim 12, wherein two blocks are situated neighboring one another and having an intermediate space to one another, so that the pipette or dispenser tips are situated along the shared line and assume a second position.

14. The method according to claim 12, wherein the blocks are situated opposite one another mirror symmetrically at a distance, so that the pipette or dispenser tips are opposite in two spaced lines and assume a third position.

15. The method according to claim 12, wherein, by regrouping the blocks, the pipette or dispenser tips—starting from the first position and leading to the second position or to the third position—perform pipetting over and distribution of samples from a 384-well microplate to 96-well microplates.

16. The method according to claim 12, wherein, by regrouping the blocks, the pipette or dispenser tips—starting from the second position or from the third position and leading to the first position—perform pipetting over and consolidation of the liquid samples from 96-well microplates to a 384-well microplate.

* * * * *